(12) United States Patent
Kondo et al.

(10) Patent No.: US 7,019,162 B2
(45) Date of Patent: Mar. 28, 2006

(54) PROCESS FOR PREPARING 2-FLUORO-3-OXOALKYLCARBOXYLIC ACID ESTER

(75) Inventors: Norihisa Kondo, Shunan (JP); Hideyuki Mimura, Shunan (JP); Kazunori Nukui, Shunan (JP); Kosuke Kawada, Kudamatsu (JP); Shoji Arai, Shunan (JP)

(73) Assignee: Tosoh F-Tech, Inc., Yamaguchi (JP)

( * ) Notice: Subject to any disclaimer, the term of this patent is extended or adjusted under 35 U.S.C. 154(b) by 0 days.

(21) Appl. No.: 10/451,814

(22) PCT Filed: Dec. 25, 2001

(86) PCT No.: PCT/JP01/11320

§ 371 (c)(1),
(2), (4) Date: Jun. 26, 2003

(87) PCT Pub. No.: WO02/051789

PCT Pub. Date: Jul. 4, 2002

(65) Prior Publication Data

US 2004/0054217 A1    Mar. 18, 2004

(30) Foreign Application Priority Data

Dec. 26, 2000  (JP) ............................. 2000-394202
Dec. 26, 2000  (JP) ............................. 2000-394203

(51) Int. Cl.
    C07C 69/66    (2006.01)
(52) U.S. Cl. ..................................... 560/184
(58) Field of Classification Search ................ 562/170; 560/170
    See application file for complete search history.

(56) References Cited

FOREIGN PATENT DOCUMENTS

| EP | 0 891 962 | 1/1999 |
|---|---|---|
| JP | 9-255611 | 9/1997 |
| JP | 2001-354622 | 12/2001 |
| WO | 97/35824 | 10/1997 |
| WO | 01/30740 | 5/2001 |

OTHER PUBLICATIONS

Chambers et al, Tetrahedron, Direct Fluorination of 1,3-Dicarbonyl Compounds, 1995, 52(1), pp. 1-8.*

* cited by examiner

*Primary Examiner*—Paul A. Zucker
(74) *Attorney, Agent, or Firm*—Wenderoth, Lind & Ponack, L.L.P.

(57) ABSTRACT

A process for producing a 2-fluoro-3-oxoalkylcarboxylic acid ester by fluorinating 3-oxoalkylcarboxylic acid ester with a fluorine gas is provided. The process is characterized in that the concentration of 3-oxoalkylcarboxylic acid ester in the reaction mixture for fluorination is maintained at 3 wt % or higher. Also provided is a process for purifying 2-fluoro-3-oxoalkylcarboxylic acid ester characterized in that 2-fluoro-3-oxoalkylcarboxylic acid ester is produced at high yield and with less impurities by washing fluorinated 3-oxoalkylcarboxylic acid ester with 3 or more times as much water as the amount of reaction mixture. According to the processes of the present invention, not only is the generation of unwanted by-products minimized, but fluorinated 3-oxoalkylcarboxylic acid ester can be purified in an efficient manner. Thus, the present invention permits efficient production of considerably pure 2-fluoro-3-oxoalkylcarboxylic acid ester, a useful intermediate material in the production of various medical and agricultural agents.

14 Claims, No Drawings

PROCESS FOR PREPARING 2-FLUORO-3-OXOALKYLCARBOXYLIC ACID ESTER

TECHNICAL FIELD

The present invention relates to a process for producing 2-fluoro-3-oxoalkylcarboxylic acid ester, an important intermediate material used in the production of various pharmaceutical or agricultural agents.

BACKGROUND ART

Fluoride-containing dicarbonyl compounds such as 2-fluoro-3-oxoalkylcarboxylic acid ester are of significant importance since they serve as an intermediate material in the production of various pharmaceutical and agricultural agents.

In some of known production processes for these compounds, certain dicarbonyl compounds are subjected to direct fluorination by fluorine gas. For example, techniques disclosed in J. Org. Chem., 57, 2196 (1992), International Patent Publication WO94/10120, International Patent Publication WO95/14646, and Japanese Patent Laid-Open Publication No. Hei 9-255611 involve direct fluorination of 3-oxoalkylcarboxylic acid ester with fluorine gas to produce desired 2-fluoro-3-oxoalkylcarboxylic acid ester.

However, such direct fluorination with fluorine gas generally involves formation of radicals and it is thus difficult to selectively obtain the desired 2-fluoro-3-oxoalkylcarboxylic acid ester alone if 3-oxoalkylcarboxylic acid ester is directly fluorinated with fluorine gas. In particular, each of the above-described fluorination processes results in formation of unwanted by-products such as monofluoro, difluoro, and polyfluorinated compounds, making the final product inappropriate to be used as a material for medical or agricultural agents. Thus, each of these processes requires some measures to purify 2-fluoro-3-oxoalkylcarboxylic acid ester.

In this regard, the aforementioned literatures only describe addition of water to wash off the hydrogen fluoride by-product, followed by extraction with an organic solvent such as dichloromethane, and none of them mention any approach to selectively remove unwanted monofluoro, difluoro, and polyfluorinated by-products from the reaction mixture and to thereby efficiently purify the intended 2-fluoro-3-oxoalkylcarboxylic acid ester. Thus, none of these techniques have reached an industrially ideal level.

In light of such situation, the present inventors made an attempt to separate the products from the reaction mixture containing differently fluorinated 3-oxoalkylcarboxylic acid esters by using a standard distillation technique. It has proven difficult, however, to purify the desired product since the polyfluorinated 3-oxoalkylcarboxylic acid esters, such as 2,5-difluoro-3-oxoalkylcarboxylic acid ester, are unstable when subjected to heat and can readily decompose to produce hydrogen fluoride.

Furthermore, polyfluorinated 3-oxoalkylcarboxylic acid esters, such as 2,4-difluoro-3-oxoalkylcarboxylic acid ester and 2,2,4-trifluoro-3-oxoalkylcarboxylic acid ester, in addition to their instability toward heat, have a structure and a molecular weight similar to those of the desired 2-fluoro-3-oxoalkylcarboxylic acid ester and are therefore difficult to efficiently purify by distillation.

For these reasons, fluorinated 3-oxoalkylcarboxylic acid esters have been used to date as a material in the subsequent processes without being subjected to purification by distillation. One such example is a technique disclosed in European Patent 0440372A1 for producing triazole derivatives, compounds often used as a fungicide. In this technique, 2-fluoro-3-oxoalkylcarboxylic acid ester is reacted with amidine. When 2-fluoro-3-oxoalkylcarboxylic acid ester containing significant amounts of by-products is used as a material for the reaction, not only is the purity of the product reduced, but compounds of unknown structure are also formed. This considerably limits the conditions for the reaction and adds to the difficulty in producing the desired product.

Accordingly, it is an objective of the present invention to provide a novel process for effectively producing a highly purified 2-fluoro-3-oxoalkylcarboxylic acid ester suitable for use as an intermediate material in the production of medical and agricultural agents. In this process, fluorination of 3-oxoalkylcarboxylic acid ester is carried out while formation of 2,5-difluoro-3-oxoalkylcarboxylic acid ester by-product is controlled and by-products such as 2,4-difluoro-3-oxoalkylcarboxylic acid ester and 2,2,4-trifluoro-3-oxyalkylcarboxylic acid ester are selectively removed.

DISCLOSURE OF THE INVENTION

In view of the above-described situation, the present inventors have conducted extensive studies and have made a finding that polyfluorinated 3-oxoalkylcarboxylic acid esters such as 2,5-difluoro-3-oxoalkylcarboxylic acid ester are rapidly formed during the late stage of the fluorination of 3-oxoalkylcarboxylic acid ester, leading to a reduction in the amount of 2-fluoro-3-oxoalkylcarboxylic acid ester.

This finding has led the present inventors to conceive an idea that, by controlling the concentration of 3-oxoalkylcarboxylic acid ester during the fluorination, the formation of 2,5-difluoro-3-oxoalkylcarboxylic acid esters can be controlled and, thus, 2-fluoro-3-oxoalkylcarboxylic acid ester can be efficiently produced. Another finding is that 2-fluoro-3-oxoalkylcarboxylic acid ester can be purified by distillation if the 2,5-difluoro-3-oxoalkylcarboxylic acid ester by-product is maintained at a low concentration.

The present inventors also discovered that the excessively fluorinated by-products such as 2,4-difluoro-3-oxoalkylcarboxylic acid ester can be selectively removed from a mixture of fluorinated 3-oxoalkylcarboxylic acid esters by repeating washing with water in addition to the washing previously provided in the conventional process, which only requires an amount of water sufficient to remove the resulting hydrogen fluoride. On the basis of this finding, the present inventors have devised a method for efficiently purifying 2-fluoro-3-oxoalkylcarboxylic acid ester at high yield by developing a washing process and a distillation process of the fluorinated 3-oxoalkylcarboxylic acid ester. The present inventors have thus completed the present invention.

In one aspect, the present invention concerns a process for producing a 2-fluoro-3-oxoalkylcarboxylic acid ester represented by the following general formula (2):

(2)

wherein $R_1$ represents alkyl or alkenyl group and R2 represents protective group of carboxyl group; the process involv ing fluorinating with fluorine gas a 3-oxoalkylcarboxylic acid ester represented by the following general formula (1):

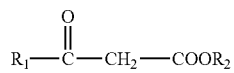
(1)

wherein $R_1$ and $R_2$ are the same as defined above. This process is characterized in that the concentration of 3-oxoalkylcarboxylic acid ester in the reaction mixture for fluorination is maintained at 3 wt % or higher. In another aspect, the present invention provides a process for producing a 2-fluoro-3-oxoalkylcarboxylic acid ester, characterized in that, following the removal of hydrogen fluoride in the aforementioned process, 2-fluoro-3-oxoalkylcarboxylic acid ester is separated from the reaction mixture by distillation. In still another aspect, the present invention provides a process for producing a 2-fluoro-3-oxoalkylcarboxylic acid ester at a high purity, characterized in that, subsequent to the fluorination, 2,4-difluoro-3-oxoalkylcarboxylic acid ester by-product is removed by washing with water, which is carried out by using at least 3 or more times as much water as the amount of reaction mixture. In still another aspect, the present invention provides a process for producing a 2-fluoro-3-oxoalkylcarboxylic acid ester at a high purity, characterized in that 2,4-difluoro-3-oxoalkylcarboxylic acid ester by-product is removed from the reaction mixture obtained in the above-described process to an amount of 5.0 wt % or less, and the above-described process is subjected to distillation under reduced pressure.

The present invention will now be described in detail.

In the present invention, 3-oxoalkylcarboxylic acid ester to serve as a reaction material is a β-dicarbonyl compound having an active methylene group and represented by the general formula (1) above.

$R_1$ in the general formula (1) represents a substituent that comprises a hydrocarbon having 1 to 10 carbon atoms, such as an alkyl group and an alkenyl group. Examples of the substituent include alkyl groups such as methyl, ethyl, propyl, isopropyl, cyclopropyl, butyl, isobutyl, hexyl, cyclohexyl, and octyl, and alkenyl groups such as propenyl, butenyl, and hexenyl. Hydrogen atoms present in the substituent $R_1$ may or may not be substituted with fluorine atoms.

$R_2$, serving as a protective group of carboxylic acid, may be any organic compound that can form an ester bond. Examples of $R_2$ include, but are not limited to, alkyl, alkenyl, and aryl groups. Examples of preferred 3-oxoalkylcarboxylic acid ester include 3-oxobutyric acid ester and 3-oxopentanoic acid ester.

Preferably, 3-oxoalkylcarboxylic acid ester of the general formula (1) forms an ester having a lower alkyl group such as a methyl ester and an ethyl ester.

A first step of the process of the present invention is to fluorinate 3-oxoalkylcarboxylic acid ester with fluorine gas.

One example is described in International Patent Publication WO95/14646, in which 3-oxoalkylcarboxylic acid ester is directly fluorinated with a fluorine gas that has been diluted with nitrogen or other inert gases. According to this approach, the fluorination step can be properly carried out to prepare a desired reaction mixture: 3-oxoalkylcarboxylic acid ester is first placed in a reactor equipped with a stirrer and a thermometer. While the ester is being stirred, bubbles of a fluorine gas diluted with nitrogen to a concentration of approximately 10% are introduced to carry out the reaction. The reaction generally takes about 5 to 40 hours at temperatures of 0 to 15° C. though the time it takes for the reaction to complete may vary depending on the amount of the reaction mixture and the rate of bubbling with fluorine gas.

Techniques for fluorination include, but are not limited to, batch processes in which fluorine gas is blown into 3-oxoalkylcarboxylic acid ester or in which a solution into which fluorine gas has been dissolved is added, as well as continuous processes in which 3-oxoalkylcarboxylic acid ester is continuously blown into a reaction container along with fluorine gas or in which 3-oxalkylcarboxylic acid ester, along with fluorine gas, is continuously passed through a reaction tube. Preferably, the amount of polyfluorinated 3-oxoalkylcarboxylic acid esters such as 2,5-difluoro-3-oxoalkylcarboxylic acid ester, which are by-products formed as a result of excessive fluorination during the fluorination process, are minimized since they can be thermally decomposed in the subsequent distillation process to produce hydrogen fluoride, which causes the decomposition of 2-fluoro-3-oxoalkylcarboxylic acid ester.

Other polyfluorinated 3-oxoalkylcarboxylic acid ester by-products other than 2,5-difluoro-3-oxoalkylcarboxylic acid ester include 2,2-difluoro-3-oxoalkylcarboxylic acid ester, 2,4-difluoro-3-oxoalkylcarboxylic acid ester, 2,2,4-trifluoro-3-oxoalkylcarboxylic acid ester, and 2,2,5-trifluoro-3-oxoalkylcarboxylic acid ester.

The rate of the reaction can be determined by sampling the reaction mixture as desired and performing gas chromatography analysis so that the concentration of 3-oxoalkylcarboxylic acid ester, serving as the material for the reaction, in the fluorination mixture is maintained 3 wt % or above, and preferably, 10 wt % or above while the molar ratio of the 2,5-difluoro-3-oxoalkylcarboxylic acid ester to 2-fluoro-3-oxoalkylcarboxylic acid ester is kept at a value of 0.05 or below, and preferably, at a value of 0.01 or below.

By maintaining the concentration of 3-oxoalkylcarboxylic acid ester in the fluorination mixture at 3 wt % or above, the generation of the polyfluorinated 3-oxoalkylcarboxylic acid ester by-products including 2,5-difluoro-3-oxoalkylcarboxylic acid ester can be minimized and, as a result, yield of 2-fluoro-3-oxoalkylcarboxylic acid ester can be increased.

If the concentration of 3-oxoalkylcarboxylic acid ester in the fluorination mixture is less than 3 wt %, then the generation of 2,5-difluoro-3-oxoalkylcarboxylic acid ester proceeds. As the molar ratio of the 2,5-difluoro-3-oxoalkylcarboxylic acid ester to 2-fluoro-3-oxoalkylcarboxylic acid ester exceeds 0.05, the resultant 2-fluoro-3-oxoalkylcarboxylic acid ester is further fluorinated to rapidly produce impurities, resulting in a reduction in the amount of 2-fluoro-3-oxoalkylcarboxylic acid ester.

A second step of the process of the present invention is to remove the hydrogen fluoride by-product from the reaction mixture obtained by the fluorination of 3-oxoalkylcarboxylic acid ester.

Among techniques for removing hydrogen fluoride from the reaction solution are one in which the reaction solution is washed with water and one in which the reaction solution is distilled under reduced pressure.

During the direct fluorination of 3-oxoalkylcarboxylic acid ester using fluorine gas, hydrogen fluoride is produced in an amount equal to that of the reacted fluorine gas. This hydrogen fluoride is typically dissolved in the reaction solution.

In general, the resultant hydrofluoric acid is removed with water in the form of hydrofluoric acid. Subsequent to the removal of fluoric acid, the process of the present invention further involves even more effective washing with water so that the unwanted by-products such as 2,4-difluoro-3-oxoalkylcarboxylic acid ester, 2,5-difluoro-3-oxoalkylcarboxylic acid ester, and 2,2,4-trifluoro-3-oxoalkylcarboxylic acid ester can be selectively eliminated.

To carry out this washing step in accordance with the present invention, a water-insoluble organic solvent may be added to the reaction mixture although the reaction mixture may be washed directly with water without using any solvent. Examples of such an organic solvent include hydrocarbons such as pentane, hexane, cyclohexane, and octane; halogenated hydrocarbons such as dichloromethane, chloroform, and 1,2-dichloroethane; aromatic compounds such as benzene, toluene, and xylene; ethers such as diethylether, diisopropylether, and diphenylether; esters such as methyl acetate, ethyl acetate, andbutyl acetate; and nitriles such as propionitrile, and butyronitrile. These organic solvents may be used either individually or as a mixture of two or more solvents.

When an organic solvent is used, the desired 2-fluoro-3-oxoalkylcarboxylic acid ester can be obtained as free a product from water soluble by-products by distilling out the organic solvent from the organic phase remaining after the washing with water.

While water may be used in the washing process in any amount that is three or more times larger than the amount of the reaction mixture, the amount of water is preferably 3 to 20 times, and more preferably, 3 to 10 times the amount of the reaction mixture.

The washing may be repeated as many times as desired by taking into consideration the amount of water used.

Although it is generally sufficient to use as much water as the reaction mixture at a time or in two portions for the purpose of washing out the hydrogen fluoride by-product alone, it is preferred to repeat the washing by using at least 3 or more times as much water as the reaction mixture in 2 to 10 portions when it is desired to selectively remove 2,4-difluoro-3-oxoalkylcarboxylic acid ester, 2,5-difluoro-3-oxoalkylcarboxylic acid ester, 2,2,4-trifluoro-3-oxoalkylcarboxylic acid ester and other by-products.

While the washing with water may be carried out at any temperature between 0 and 60° C., it is preferably carried out at temperatures of 5 to 40° C.

The additional washings following the removal of the hydrofluoric acid can selectively reduce the 2,4-difluoro-3-oxoalkylcarboxylic acid ester, an unwanted impurity, present in the resulting mixture that also contains 2-fluoro-3-oxoalkylcarboxylic acid ester down to as small an amount as 5 wt % or less, despite the fact that 2,4-difluoro-3-oxoalkylcarboxylic acid ester has the physical and chemical properties similar to those of 2-fluoro-3-oxoalkylcarboxylic acid ester. The resulting mixture can thus be used directly as a material in ring formation or other chemical reactions for producing medical and agricultural agents.

The distillation under reduced pressure for removing hydrogen fluoride may be carried out by maintaining the reaction mixture at temperatures of 50° C. or below, and more preferably, at temperatures of 40° C. or below. In this manner, hydrogen fluoride can be effectively removed. The distillation is carried out while the pressure is gradually decreased from atmospheric pressure to about 4.00 Kpa (30 torr) depending on the amount of hydrogen fluoride present. The distillation process is typically carried out in 3 to 15 hours while it may take any length of time.

Another technique used for the removal of hydrogen fluoride is distillation using an azeotropic agent to form an azeotrope. Examples of the compound that can form an azeotrope with hydrogen fluoride include ethers such as dimethylether, diethylether, diisopropylether; fluorinated hydrochlorocarbons such as trifluoroethylchloride, Freon-12, and Freon-22; and hydrocarbons such as butane and isobutane. The azeotropic agent may be added to the reaction mixture or, alternatively, bubbles of the azeotropic agent may be continuously introduced into the mixture.

In addition to the above-described processes for removing hydrogen fluoride, a basic compound may optionally be added to the reaction mixture to further enhance the removal of hydrogen fluoride. Such compounds include hydroxides, carbonates, and bicarbonates of alkali metals and alkali earth metals.

Hydrogen fluoride is preferably removed as much as possible and is typically reduced to 2.0 wt % or less and, preferably, to 1.0 wt % or less with respect to the amount of the reaction mixture. The reaction mixture containing 2.0 wt % or more of hydrogen fluoride is unfavorable since such a mixture can lead to a decrease in the purity and yield of the resulting 2-fluoro-3-oxoalkylcarboxylic acid ester when subjected to the subsequent separation process by distillation.

The next step in the process of the present invention is to distill the reaction mixture from which hydrogen fluoride has been removed and separate 2-fluoro-3-oxoalkylcarboxylic acid ester, a desired product.

Once the 2,4-difluoro-3-oxoalkylcarboxylic acid ester, which has a boiling point close to that of 2-fluoro-3-oxoalkylcarboxylic acid ester, has been reduced through washing with water to an amount of 5 wt % or less, the mixture containing 2-fluoro-3-oxoalkylcarboxylic acid ester can further be purified by distillation.

If the mixture containing 2-fluoro-3-oxoalkylcarboxylic acid ester contains 5 wt % or more of 2,4-difluoro-3-oxoalkylcarboxylic acid ester, not only do their close boiling points make the purification process by distillation difficult, but also the decomposition of 2,4-difluoro-3-oxoalkylcarboxylic acid ester is increased. As a result, the yield of 2-fluoro-3-oxoalkylcarboxylic acid ester with a purity of 95 wt % or higher, which is obtained as the main fraction, is significantly reduced.

Distillation under reduced pressure is suited for the purpose of purifying 2-fluoro-3-oxoalkylcarboxylic acid ester. This process is preferably carried out under a pressure of 4.00 KPa (30 torr) or lower and at temperatures of 150° C. or lower, more preferably at temperatures of 130° C. or lower, and still more preferably at temperatures of 125° C. or lower, while temperatures are preferably kept as low as possible. If the temperature exceeds 150° C., 3-oxoalkylcarboxylic acid ester, as well as fluorinated derivatives thereof, tends to become unstable and may become susceptible to decomposition.

Some of 3-oxoalkylcarboxylic acid ester is left unreacted when the fluorination process is terminated at an early stage. The step of purification by distillation helps prevent this 3-oxoalkylcarboxylic acid ester from contaminating the product. Also, 3-oxoalkylcarboxylic acid ester separated in the purification step may be returned to the fluorination step for recycling.

In this manner, the desired 2-fluoro-3-oxoalkylcarboxylic acid ester with a high purity can be produced efficiently.

BEST MODES FOR CARRYING OUT THE INVENTION

The present invention will now be described in more detail with reference to examples, which are not intended to limit the scope of the invention in any way. The names and respective acronyms of the compounds used in Examples and Comparative Examples are as follows:

MOP: methyl ester of 3-oxopentanoic acid
MFOP: methyl ester of 2-fluoro-3-oxopentanoic acid
2,5-DFOP: methyl ester of 2,5-difluoro-3-oxopentanoic acid
2,2-DFOP: methyl ester of 2,2-difluoro-3-oxopentanoic acid
2,4-DFOP: methyl ester of 2,4-difluoro-3-oxopentanoic acid
2,2,4-TFOP: methyl ester of 2,2,4-trifluoro-3-oxopentanoic acid.

EXAMPLE 1

5000 g MOP was placed in a 10 L stainless-steel reactor equipped with a thermometer and a stirrer. Bubbles of 10% fluorine gas diluted with nitrogen were introduced into the reactor to carry out the reaction. The reaction was allowed to proceed for 19 hours while the temperature was maintained at 10° C. The reaction was then terminated and the resulting reaction mixture was analyzed by gas chromatography (PEG 20M, 3 m and OV-1, 3 m). The results of the analysis revealed that the crude product obtained through the reaction contained 3.7 wt % MOP, 43.8 wt % MFOP, 5.2 wt % 2,2-DFOP, 21.9 wt % 2,4-DFOP, 2.2 wt % 2,5-DFOP, 1.1 wt % 2,2,4-TFOP, and 13.3 wt % hydrogen fluoride (HF). The molar ratio of 2,5-DFOP to MFOP was 0.04.

EXAMPLE 2

To completely remove the hydrofluoric acid by-product from the fluorinated reaction mixture obtained in Example 1, the reaction mixture was transferred to a polyethylene separating funnel. To 1 kg of the fluorinated reaction mixture, approximately 1 L of water and approximately 1 L of chloroform were added. The resulting mixture was thoroughly shaken at room temperature (15–20° C.) and was then allowed to stand still until the mixture was separated into two layers. Subsequently, approximately 1 L of additional water was added to the chloroform layer and the same process was repeated. This washing process was repeated 4 times in total. After washing, the solvent was removed from the chloroform layer by distillation to obtain a crude product, which was then subjected to gas chromatography analysis. The results of the analysis revealed that the washed product was composed of 5.3 wt % MOP, 85.0 wt % MFOP, 7.8 wt % 2,2-DFOP, 1.5 wt % 2,4-DFOP, 0.4 wt % 2,5-DFOP, 0.0 wt % 2,2,4-TFOP, and 0.0 wt % HF. The weight of the product remaining after 4 times of the washing was about 456 g.

EXAMPLE 3

The process was carried out in the same manner as in Example 2, except that the reaction mixture from which hydrofluoric acid had been completely removed was washed with water 6 times in total. The results of the gas chromatography analysis performed on the resulting product revealed that the washed product was composed of 4.7 wt % MOP, 87.8 wt % MFOP, 7.1 wt % 2,2-DFOP, 0.3 wt % 2,4-DFOP, 0.1 wt % 2,5-DFOP, 0.0 wt % 2,2,4-TFOP, and 0.0 wt % HF. The weight of the product remaining after 6 times of the washing was about 416 g.

EXAMPLE 4

The process was carried out in the same manner as in Example 2, except that the washing of the fluorinated reaction mixture was carried out at temperatures of 5 to 10° C. The results of the gas chromatography analysis performed on the resulting product revealed that the washed product was composed of 5.3 wt % MOP, 85.5 wt % MFOP, 7.6 wt % 2,2-DFOP, 0.7 wt % 2,4-DFOP, 0.8 wt %2,5-DFOP, 0.0 wt %2,2,4-TFOP, and 0.0 wt % HF. The weight of the product remaining after 4 times of the washing was about 461 g.

COMPARATIVE EXAMPLE 1

To completely remove the hydrofluoric acid by-product from the fluorinated reaction mixture obtained in Example 1, the reaction mixture was transferred to a polyethylene separating funnel. To 1 kg of the fluorinated reaction mixture, approximately 1 L of water and approximately 1 L of chloroform were added. The resulting mixture was thoroughly shaken at room temperature (15–20° C.) and was then allowed to stand still until the mixture was separated into two layers. After washing, the solvent was removed from the chloroform layer by distillation to obtain a crude product, which was then subjected to gas chromatography analysis. The results of the analysis revealed that the washed product was composed of 5.4 wt % MOP, 69.7 wt % MFOP, 7.8 wt % 2,2-DFOP, 15.1 wt % 2,4-DFOP, 2.0 wt % 2,5-DFOP, 0.2 wt % 2,2,4-TFOP, and 0.0 wt % HF. The weight of the crude product remaining after the washing to remove hydrofluoric acid was about 611 g.

COMPARATIVE EXAMPLE 2

The process was carried out in the same manner as in Comparative Example 1, except that another 1 L of water was added to the reaction mixture after the removal of hydrofluoric acid for an additional washing. The results of the gas chromatography analysis performed on the resulting product revealed that the washed product was composed of 5.6 wt % MOP, 77.8 wt % MFOP, 8.1 wt % 2,2-DFOP, 7.3 wt % 2,4-DFOP, 1.2 wt % 2,5-DFOP, 0.0 wt % 2,2,4-TFOP, and 0.0 wt % HF. The weight of the crude product remaining after the washing was about 530 g.

EXAMPLE 5

120 g of the liquid obtained in Example 2 in a still was subjected to a batch distillation process in which the pressure was first reduced from atmospheric pressure to 2.67 KPa (20 torr) with the still temperature maintained at 103° C. and after 4 hours, the pressure was further reduced to 1.33 KPa (10 torr) with the still temperature maintained at 87° C. The distillation was ended after 16 hours. In this manner, the liquid was separated into four fractions: a first fraction composed mainly of low-boiling point products; a fraction composed mainly of MOP; a main fraction composed mainly of MFOP (purity of MFOP=95 wt % or higher); and a residual fraction remaining in the still and composed mainly of high-boiling point products. Each fraction was then analyzed by gas chromatography to determine the concentration of MFOP. The first fraction weighed 8.1 g and contained 0.8 wt % of MFOP. The fraction composed mainly of MOP weighed 5.0 g and contained 14.6 wt % MFOP. The fraction composed mainly of MFOP weighed 85.2 g and contained 98.2 wt % MFOP. The residual fraction, weighing 21.7 g, contained 16.2 wt % MFOP. The material balance of MFOP was 98 wt %, indicating little decomposition of the compound.

COMPARATIVE EXAMPLE 3

Purification process by distillation was carried out in the same manner as in Example 5, except that 120 g of the liquid obtained in Comparative Example 2 in a still was used. The liquid was separated into four fractions: a first fraction composed mainly of low-boiling point products; a main fraction composed mainly of MOP; a fraction composed mainly of MFOP (purity of MFOP=95 wt % or higher); and a residual fraction remaining in the still and composed mainly of high-boiling point products. Each fraction was then analyzed by gas chromatography to determine the concentration of MFOP. The first fraction weighed 7.9 g and contained 0.7 wt % of MFOP. The fraction composed mainly of MOP weighed 5.4 g and contained 11.7 wt % MFOP. The fraction composed mainly of MFOP weighed 43.2 g and contained 95.0 wt % MFOP. The residual fraction, weighing 63.5 g, contained 57.0 wt % MFOP. Coloring of the liquid in the still, decomposition of the composition, and generation of heavy fraction were observed over the course of the distillation process and the material balance of MFOP was decreased to 92 wt %.

EXAMPLE 6

As with Example 1, 5000 g MOP was loaded and bubbles of 10 wt % fluorine gas diluted with nitrogen were introduced into the reactor to carry out the reaction. The reaction was allowed to proceed for 12 hours while the temperature was maintained at 5° C. The reaction was then terminated and the resulting reaction mixture was analyzed by gas chromatography (PEG 20M, 3 m and OV-1, 3 m). The results of the analysis revealed that the crude product obtained through the reaction contained 14.6 wt % MOP, 43.2 wt % MFOP, 4.9 wt % 2,2-DFOP, 20.8 wt % 2,4-DFOP, 0.5 wt % 2,5-DFOP, 0.3 wt % 2,2,4-TFOP, and 13.1 wt % hydrogen fluoride (HF). The molar ratio of 2,5-DFOP to MFOP was 0.01.

As with Examples 2, to 1 kg of the resulting fluorinated reaction mixture, approximately 1 L water and approximately 1 L chloroform were added. The resulting mixture was thoroughly shaken at room temperature (15–20° C.) and was then allowed to stand still until the mixture was separated into two layers. Subsequently, approximately 1 L of additional water was added to the chloroform layer and the same process was repeated. This washing process was repeated 4 times in total. After washing, the chloroform layer was heated to about 40 to 60° C. while bubbles of small amounts of nitrogen were introduced thereinto. The pressure was then reduced to 26.7 KPa (200 torr) to remove chloroform by distillation.

Subsequently, the obtained liquid in a still was subjected to a batch distillation process in the same manner as in Example 5 in which the pressure was first reduced from atmospheric pressure to 2.67 KPa (20 torr) with the still temperature maintained at 103° C. and after 4 hours, the pressure was further reduced to 1.33 KPa (10 torr) with the still temperature maintained at 87° C. The distillation was ended after 16 hours. In this manner, the liquid was separated into four fractions: a first fraction composed mainly of low-boiling point products; a fraction composed mainly of MOP; a main fraction composed mainly of MFOP (purity of MFOP=95 wt % or higher); and a residual fraction remaining in the still and composed mainly of high-boiling point products. Each fraction was then analyzed by gas chromatography to determine the concentration of MFOP. The first fraction weighed 10.3 g and contained 0.6 wt % of MFOP. The fraction composed mainly of MOP weighed 21.3 g and contained 5.5 wt % MFOP. The fraction composed mainly of MFOP weighed 80.2 g and contained 95.3 wt % MFOP. The residual fraction, weighing 8.2 g, contained 23.5 wt % MFOP. The material balance of MFOP was 99 wt %, indicating little decomposition of the compound.

COMPARATIVE EXAMPLE 4

As with Example 1, 5000 g MOP was loaded and bubbles of 10% fluorine gas diluted with nitrogen were introduced into the reactor to carry out the reaction. The reaction was allowed to proceed for 28 hours while the temperature was maintained at 10° C. The reaction was then terminated and the resulting reaction mixture was analyzed by gas chromatography (PEG 20M, 3 m and OV-1, 3 m). The results of the analysis revealed that the crude product obtained through the reaction contained 0.4 wt % MOP, 29.0 wt % MFOP, 8.0 wt % 2,2-DFOP, 18.5 wt % 2,4-DFOP, 10.1 wt % 2,5-DFOP, 5.0 wt % 2,2,4-TFOP, and 18.0 wt % hydrogen fluoride (HF). The molar ratio of 2,5-DFOP to MFOP was 0.31.

As with Examples 2, to 1kg of the resulting fluorinated reaction mixture, approximately 1 L water and approximately 1 L chloroform were added, and the resulting mixture was thoroughly shaken at room temperature (15–20° C.) and was then allowed to stand still until the mixture was separated into two layers. Subsequently, approximately 1 L of additional water was added to the chloroform layer and the same process was repeated. This washing process was repeated 4 times in total. After washing, the chloroform layer was heated to about 40 to 60° C. while bubbles of small amounts of nitrogen were introduced thereinto. The pressure was then reduced to 26.7 KPa (200 torr) to remove chloroform by distillation.

Subsequently, the obtained liquid in a still was subjected to a batch distillation process in the same manner as in Example 5 in which the pressure was first reduced from atmospheric pressure to 2.67 KPa (20 torr) with the still temperature maintained at 103° C. and after 4 hours, the pressure was further reduced to 1.33 KPa (10 torr) with the still temperature maintained at 87° C. The distillation was ended after 13 hours. In this manner, the liquid was separated into four fractions: a first fraction composed mainly of low-boiling point products; a fraction composed mainly of MOP; a main fraction composed mainly of MFOP; and a residual fraction remaining in the still and composed mainly of high-boiling point products. Each fraction was then analyzed by gas chromatography to determine the concentration of MFOP. The first fraction weighed 15.9 g and contained 2.9 wt % of MFOP. The fraction composed mainly of MOP weighed 3.1 g and contained 13.5 wt % MFOP. The fraction composed mainly of MFOP weighed 48.7 g and contained 98.8 wt % MFOP. The residual fraction, weighing 52.2 g, contained 16.0 wt % MFOP. Coloring of the liquid in the still, decomposition of the composition, and generation of heavy fraction were observed over the course of the distillation process and the material balance of MFOP was decreased to 85 wt %.

COMPARATIVE EXAMPLE 5

As with Example 1, 5000 g MOP was loaded and bubbles of 10% fluorine gas diluted with nitrogen were introduced into the reactor to carry out the reaction. The reaction was allowed to proceed for 32 hours while the temperature was maintained at 0° C. The reaction was then terminated and the resulting reaction mixture was analyzed by gas chromatography (PEG 20M, 3 m and OV-1, 3 m). The results of the analysis revealed that the crude product obtained through the reaction contained 1.3 wt % MOP, 39.2 wt % MFOP, 7.1 wt % 2,2-DFOP, 22.9 wt % 2,4-DFOP, 6.0 wt % 2,5-DFOP, 3.0 wt % 2,2,4-TFOP, and 16.3 wt % hydrogen fluoride (HF). The molar ratio of 2,5-DFOP to MFOP was 0.14.

As with Examples 2, to 1 kg of the resulting fluorinated reaction mixture, approximately 1 L water and approximately 1 L chloroform were added. The resulting mixture was thoroughly shaken at room temperature (15–20° C.) and was then allowed to stand still until the mixture was separated into two layers. Subsequently, approximately 1 L of additional water was added to the chloroform layer and the same process was repeated. This washing process was repeated 4 times in total. After washing, the chloroform layer was heated to about 40 to 60° C. while bubbles of small amounts of nitrogen were introduced thereinto. The pressure was then reduced to 26.7 KPa (200 torr) to remove chloroform by distillation.

Subsequently, the liquid remaining in a still that was obtained in the same manner as in Example 5 was subjected to a batch distillation process in which the pressure was first reduced from atmospheric pressure to 2.67 KPa (20 torr) with the still temperature maintained at 103° C. and after 4 hours, the pressure was further reduced to 1.33 KPa (10 torr) with the still temperature maintained at 87° C. The distillation was ended after 15 hours. In this manner, the liquid was separated into four fractions: a first fraction composed mainly of low-boiling point products; a fraction composed mainly of MOP; a main fraction composed mainly of MFOP; and a residual fraction remaining in the still and composed mainly of high-boiling point products. Each fraction was then analyzed by gas chromatography to determine the concentration of MFOP. The first fraction weighed 15.5 g and contained 0.3 wt % of MFOP. The fraction composed mainly of MOP weighed 2.4 g and contained 26.2 wt % MFOP. The fraction composed mainly of MFOP weighed 71.1 g and contained 98.5 wt % MFOP. The residual fraction, weighing 31.1 g, contained 23.1 wt % MFOP. Coloring of the liquid in the still, decomposition of the composition, and generation of heavy fraction were observed over the course of the distillation process and the material balance of MFOP was decreased to 92 wt %.

INDUSTRIAL APPLICABILITY

To date, fluorinated 3-oxoalkylcarboxylic acid ester has been directly put to use without being subjected to purification processes since it contains different fluorinated products as impurities and is thus difficult to be produced in a selective manner. The present invention makes it possible to control the generation of excessively fluorinated impurities such as 2,5-difluoro-3-oxoalkylcarboxylic acid ester, thereby permitting highly selective production of considerably pure 2-fluoro-3-oxoalkylcarboxylic acid ester, which is an important intermediate material in the production of various medical and agricultural agents.

Furthermore, the present invention makes it possible to selectively remove unwanted by-products generated during fluorination of 3-oxoalkylcarboxylic acid ester by fluorine gas, such as 2,4-difluoro-3-oxoalkylcarboxylic acid ester, 2,5-difluoro-3-oxoalkylcarboxylic acid ester, and 2,2,4-trifluoro-3-oxoalkylcarboxylic acid ester, so that 2-fluoro-3-oxoalkylcarboxylic acid ester can be purified at high efficiency.

Accordingly, the present invention brings about significant improvements in the quality of pharmaceutical agents derived from 2-fluoro-3-oxoalkylcarboxylic acid ester as well as a significant reduction in the production cost and thus can lead to a substantial economic impact.

What is claimed is:

1. A process for producing a 2-fluoro-3-oxoalkylcarboxylic acid ester represented by the following general formula (2):

(2)

wherein $R_1$ represents alkyl or alkenyl group and $R_2$ represents a protective group of carboxyl group, which consists of fluorinating with fluorine gas a 3-oxoalkylcarboxylic acid ester represented by the following general formula (1):

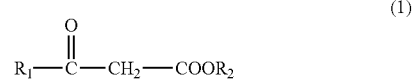

(1)

wherein $R_1$ and $R_2$ are the same as defined above, wherein a concentration of the 3-oxoalkylcarboxylic acid ester in a reaction mixture for fluorination is maintained at 3 wt % or higher, while formation of 2,5-difluoro-3-oxoalkylcarboxylic acid ester is controlled and 2,4-difluoro-3-oxoalkylcarboxylic acid ester and 2,2,4-trifluoro-3-oxyalkylcarboxylic acid ester are selectively removed.

2. A process for producing at a high purity a 2-fluoro-3-oxoalkylcarboxylic acid ester represented by the following general formula (2):

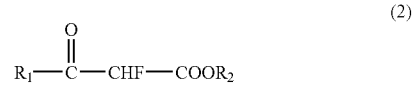

(2)

wherein $R_1$ represents alkyl or alkenyl group and $R_2$ represents a protective group of carboxyl group, which comprises fluorinating with fluorine gas a 3-oxoalkylcarboxylic acid ester represented by the following general formula (1):

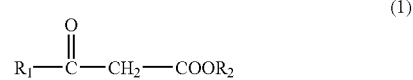

(1)

wherein $R_1$ and $R_2$ are the same as defined above, wherein subsequent to the fluorination, a 2,4-difluoro-3-oxoalkylcarboxylic acid ester by-product is removed by washing with water, wherein the washing is carried out by using water in an amount that is at least 3 or more times larger than the amount of reaction mixture.

3. A process for producing at a high purity a 2-fluoro-3-oxoalkylcarboxylic acid ester, wherein the 2,4-difluoro-3-oxoalkylcarboxylic acid ester by-product is removed from a reaction mixture obtained in the process of claim 2 by washing with water to an amount of 5.0 wt % or less.

4. A process for producing at a high purity a 2-fluoro-3-oxoalkylcarboxylic acid ester, wherein a reaction mixture obtained in the process of claim 1 from which hydrogen fluoride has been removed is subjected to distillation under reduced pressure.

5. The process according to claim 1, wherein the 3-oxoalkylcarboxylic acid ester is a lower alkyl ester of 3-oxobutylic acid or 3-oxopentanoic acid.

6. A process for producing at a high purity a 2-fluoro-3-oxoalkylcarboxylic acid ester, wherein a reaction mixture obtained in the process of claim 3 is subjected to distillation under reduced pressure.

7. The process according to claim 2, wherein the 3-oxoalkylcarboxylic acid ester is a lower alkyl ester of 3-oxobutylic acid or 3-oxopentanoic acid.

8. The process according to claim 3, wherein the 3-oxoalkylcarboxylic acid ester is a lower alkyl ester of 3-oxobutylic acid or 3-oxopentanoic acid.

9. The process according to claim 4, wherein the 3-oxoalkylcarboxylic acid ester is a lower alkyl ester of 3-oxobutylic acid or 3-oxopentanoic acid.

10. The process according to claim 6, wherein the 3-oxoalkylcarboxylic acid ester is a lower alkyl ester of 3-oxobutylic acid or 3-oxopentanoic acid.

11. The process according to claim 1, wherein the 3-oxoalkylcarboxylic acid ester is directly fluorinated in the absence of a solvent for the 3-oxoalkylcarboxylic acid ester.

12. The process according to claim 2, wherein the 3-oxoalkylcarboxylic acid ester is directly fluorinated in the absence of a solvent for the 3-oxoalkylcarboxylic acid ester.

13. The process according to claim 1, which further consists of purifying the 2-fluoro-3-oxoalkylcarboxylic acid ester.

14. The process according to claim 1, which further consists of removing hydrogen fluoride from the reaction mixture.

* * * * *